(12) United States Patent
Freeman et al.

(10) Patent No.: US 7,385,695 B2
(45) Date of Patent: Jun. 10, 2008

(54) POLARIMETRY

(75) Inventors: Neville John Freeman, Tarporley (GB); Gerard Anthony Ronan, Manchester (GB)

(73) Assignee: Fairfield Sensors Limited, Salford (GB)

( * ) Notice: Subject to any disclaimer, the term of this patent is extended or adjusted under 35 U.S.C. 154(b) by 280 days.

(21) Appl. No.: 10/497,372

(22) PCT Filed: Jan. 20, 2003

(86) PCT No.: PCT/GB03/00230

§ 371 (c)(1),
(2), (4) Date: Dec. 9, 2004

(87) PCT Pub. No.: WO03/078980

PCT Pub. Date: Sep. 25, 2003

(65) Prior Publication Data

US 2005/0088650 A1    Apr. 28, 2005

(30) Foreign Application Priority Data

Mar. 14, 2002    (GB) ................................. 0206011.9

(51) Int. Cl.
*G01J 4/00* (2006.01)
(52) U.S. Cl. ...................................... 356/364; 356/367
(58) Field of Classification Search ................ 356/367, 356/364
See application file for complete search history.

(56) References Cited

U.S. PATENT DOCUMENTS

| | | | | |
|---|---|---|---|---|
| 4,950,074 A | * | 8/1990 | Fabricius et al. ............ | 356/133 |
| 5,073,024 A | * | 12/1991 | Valette et al. ............... | 356/481 |
| 5,120,131 A | * | 6/1992 | Lukosz ........................ | 356/481 |
| 5,822,067 A | * | 10/1998 | Yanik .......................... | 356/368 |
| 6,335,793 B1 | * | 1/2002 | Freeman et al. ............. | 356/477 |

FOREIGN PATENT DOCUMENTS

| | | |
|---|---|---|
| DE | 4133128 A | 4/1993 |
| GB | 2181231 A | 4/1987 |

OTHER PUBLICATIONS

International Search Report for PCT/GB03/00230 mailed May 27, 2003; ISA/EPO.

* cited by examiner

*Primary Examiner*—Roy M Punnoose
(74) *Attorney, Agent, or Firm*—Harness, Dickey & Pierce, P.L.C.

(57) ABSTRACT

The present invention relates to an assembly and method for measuring the optical activity of a stimulus of interest. The assembly comprises a source of incident electromagnetic radiation (1), a lens arrangement (2), an input polariser (3), a planar waveguide structure (4) (or an optical fiber), an output polariser (5), a lens arrangement (6) for focussing the output electromagnetic radiation and a detector. The polarisation of the incident electromagnetic radiation relative to the planar waveguide structure (4) is determined by the input polariser (3). The planar waveguide structure in this embodiment comprises a silicon substrate layer (4c) and an absorbent layer (4e). The silicon oxynitride layer (4c) acts as the reference waveguide and the absorbent layer (4e) acts as the sensing waveguide. The sensing waveguide (4e) is exposed in the localised environment (8) to a sample containing the stimulus of interest which is optically active. The adjusted attitude of the output polariser (5) is directly proportional to the optical activity of the stimulus of interest.

23 Claims, 3 Drawing Sheets

US 7,385,695 B2

POLARIMETRY

CROSS-REFERENCE TO RELATED APPLICATIONS

This application is a National Stage of International Application No. PCT/GB03/00230, filed on Jan. 20, 2003. This application claims the benefit of Great Britain Patent Application No. 0206011.9, filed Mar. 14, 2002. The disclosures of the above applications are incorporated herein by reference.

FIELD

The present invention relates to an assembly and method for measuring the optical activity of a stimulus of interest.

BACKGROUND

Measurements of the degree of rotation of plane polarised light by a sample as a function of wavelength and concentration are important in inter alia the field of biology and biological research. Such measurements of optical activity have formed the basis of optical polarimetry utilised to assess chirality and optical isomerism for over a century and remain important as (in most other respects) optical isomers have identical properties which in general makes them difficult to distinguish or separate. For example, such measurements enable a biologically active optical isomer to be distinguished from its complementary optical isomer which may be biologically inactive.

Techniques relating to optical activity have been extended to include inter alia circular dichroism (CD) spectroscopy in which the behaviour of circularly polarised light is analysed at different wavelengths. When such wavelengths are in the UV region, important data relating (for example) to the structure and folding of proteins can be deduced. This is because the different tertiary structures adopted by protein molecules (especially alpha helical and beta pleated sheets) tend to be asymmetrical and have intrinsic optical properties which can be differentiated in terms of their optical activity. Whilst such data is very useful, its analysis is subject to some ambiguity.

SUMMARY

The present invention seeks to improve the measurement of the optical activity of chemical or biological stimuli by exploiting the response of certain optical components such as waveguide structures to which the stimuli are exposed.

Thus viewed from one aspect the present invention provides an assembly for measuring the optical activity of a stimulus of interest in a localised environment, said assembly comprising:

a source of incident electromagnetic radiation;
an input polariser for orienting the incident electromagnetic radiation into a first degree of polarisation;
an optical component capable of exhibiting a measurable response to a change in the degree of polarisation of the incident electromagnetic radiation into output electromagnetic radiation having a second degree of polarisation caused by the introduction of or changes in the stimulus of interest in the localised environment;
means for measuring the measurable response; and
means for relating the measurable response to the optical activity of the stimulus of interest.

The optical activity of the stimulus of interest measured in accordance with the invention may be advantageously used to deduce its structural, conformational, biological or chemical properties (or changes therein). For example, the optical activity may be used to deduce the chirality of the stimulus of interest.

The assembly of the invention may advantageously be used to measure the optical activity of a chemical stimulus contained in an analyte which is introduced into the localised environment. For example, a gaseous, vapour or liquid phase analyte comprising chemical stimuli may be introduced into the localised environment. Alternatively, a chemical reaction or interaction may take place which effects changes in the nature of the chemical stimuli in situ (ie causes a change in the localised environment) which can be deduced from changes in the optical activity measured in accordance with the invention.

The assembly of the invention may advantageously be used to measure the optical activity of a biological stimulus such as an enzyme, DNA fragment, protein, antibody or whole cell contained in an analyte which is introduced into the localised environment. Alternatively a change in the localised environment may be brought about by (for example) conformational changes in a biological stimulus (eg a change in the folding of a protein) which can be deduced from changes in the optical activity measured in accordance with the invention. Such conformational changes may be caused by (for example) an increase in temperature.

The stimulus of interest in the localised environment may be close to, in contact with, immobilised or bound to the optical component in any convenient manner.

The input polariser may be an input plane polariser (ie for orienting the incident electromagnetic radiation into a first degree of plane polarisation). For example, the input polariser may be a polarising filter or prism.

Preferably the assembly further comprises: a lens arrangement capable of focussing the incident electromagnetic radiation.

Preferably the assembly further comprises: a lens arrangement capable of focussing the output electromagnetic radiation.

Preferably the means for relating the measurable response to the optical activity of the stimulus of interest comprises: an output polariser for orienting the degree of polarisation of the output electromagnetic radiation.

Preferably the output polariser is an output plane polariser. The output polariser may comprise a prism.

The optical component may be an optical fibre. Typically an optical fibre would be enclosed in cladding and the localised environment may be created by removing a portion of the cladding to expose the fibre surface.

In a preferred embodiment, the optical component is a polarisation maintaining optical component. An example is a polarisation maintaining optical fibre.

In a preferred embodiment, the optical component is a waveguide structure. The waveguide structure preferably includes either (1) one or more sensing layers capable of inducing in a secondary waveguide a measurable response to a change in the degree of polarization of the incident electromagnetic radiation into output electromagnetic radiation having a second degree of polarization caused by the introduction of or changes in the stimulus of interest in the localized environment or (2) a sensing waveguide capable of exhibiting a measurable response to a change in the degree of polarization of the incident electromagnetic radiation into output electromagnetic radiation having a second degree of polarization caused by the introduction of or changes in the stimulus of interest in the localized environment.

The measurable response may be or relate to a change in the intensity (eg the total intensity) of the output electromagnetic radiation. For example, this may be measurable by coupling the output electromagnetic radiation into free space and generating an interference pattern. The interference pattern may be measured in a conventional manner. For example, the interference fringes may be measured either using a single detector which measures changes in the output electromagnetic radiation intensity or a plurality of such detectors which monitor the changes in intensity occurring in a number of fringes or the entire interference pattern. The one or more detectors may be one or more photodetectors. For the most sensitive performance, the (or each) photodetector is a photomultiplier tube capable of counting photons. Where more than one photodetector is used this may be arranged in an array.

Preferably the assembly of the invention wherein the optical component is a waveguide structure is adapted so as to be usable in evanescent mode or whole waveguide mode.

Thus in a first preferred embodiment of the invention, the optical component includes one or more sensing layers capable of inducing in a secondary waveguide a measurable response to a change in the degree of polarisation of the incident electromagnetic radiation into output electromagnetic radiation having a second degree of polarisation caused by the introduction of or changes in the stimulus of interest in the localised environment. In this first embodiment, the assembly is advantageously adapted to optimise the evanescent component.

Preferably the (or each) sensing layer comprises an absorbent material (eg a polymeric material such as polymethylmethacrylate, polysiloxane, poly-4-vinylpyridine) or a bioactive material (eg containing antibodies, enzymes, DNA fragments, functional proteins or whole cells). The absorbent material may be capable of absorbing (or capturing) a gas, a liquid or a vapour analyte containing a chemical stimulus of interest, The (or each) sensing layer may comprise a porous silicon material optionally biofunctionalised with antibodies, enzymes, DNA fragments, functional proteins or whole cells.

In a preferred assembly of the invention, the secondary waveguide comprises silicon oxynitride or silicon nitride.

In a second preferred embodiment of the invention, the optical component includes a sensing waveguide capable of exhibiting a measurable response to a change in the degree of polarisation of the incident electromagnetic radiation into output electromagnetic radiation having a second degree of polarisation caused by the introduction of or changes in the stimulus of interest in the localised environment. In this second embodiment, the assembly is adapted to minimise the evanescent component and may be used advantageously in whole waveguide mode.

Preferably the sensing waveguide comprises an absorbent material (eg a polymeric material such as polymethylmethacrylate, polysiloxane, poly-4-vinylpyridine) or a bioactive material (eg containing antibodies, enzymes, DNA fragments, functional proteins or whole cells). The absorbent material may be capable of absorbing (or capturing) a gas, a liquid or a vapour analyte containing a chemical stimulus of interest. The sensing waveguide may comprise a porous silicon material optionally biofunctionalised with antibodies, enzymes, DNA fragments, functional proteins or whole cells.

Where the optical component of the assembly of the invention comprises a sensing waveguide adapted for use in whole waveguide mode, an absorbent layer in the form of an overcoating may be present for use as a membrane (for example) to separate out stimuli of interest.

To optimise the performance of the first preferred embodiment, the optical component may further comprise an inactive secondary waveguide in which the sensing layer is incapable of inducing a measurable response to a change in the degree of polarisation of the incident electromagnetic radiation into output electromagnetic radiation having a second degree of polarisation caused by the introduction of or changes in the stimulus of interest in the localised environment. The inactive secondary waveguide is capable of acting as a reference layer. It is preferred that the secondary waveguide and inactive secondary waveguide have identical properties with the exception of the measurable response to a change in the degree of polarisation of the incident electromagnetic radiation into output electromagnetic radiation having a second degree of polarisation caused by the introduction of or changes in the stimulus of interest in the localised environment. By way of example, the secondary waveguide and inactive secondary waveguide are made of silicon oxynitride.

To optimise the performance of the second preferred embodiment, the optical component may further comprise an inactive (eg deactivated) waveguide substantially incapable of exhibiting a measurable response to a change in the degree of polarisation of the incident electromagnetic radiation into output electromagnetic radiation having a second degree of polarisation caused by the introduction of or changes in the stimulus of interest in the localised environment. The inactive waveguide is capable of acting as a reference layer. The physical, biological and chemical properties of the sensing waveguide and inactive waveguide are as similar as possible (with the exception of the response to a change in the degree of polarisation of the incident electromagnetic radiation into output electromagnetic radiation having a second degree of polarisation caused by the introduction of or changes in the stimulus of interest in the localised environment). Typically the inactive waveguide is made of silicon oxynitride.

Preferably each of the sensing waveguide and secondary waveguide (and of any additional waveguides such as a reference waveguide) of the optical component is a planar waveguide (ie a waveguide which permits light propagation in any arbitrary direction within the plane).

Preferably the waveguide structure constitutes a multi-layered structure (eg a laminated waveguide structure). In this sense, the waveguide structure is simple to fabricate and fault tolerant in terms of construction errors. In a preferred embodiment, the plurality of layers in the multi-layered optical component are built onto a substrate (eg of silicon) through known processes such as vapour deposition (eg PECVD or LPCVD). Such processes are highly repeatable and lead to accurate manufacture. Intermediate transparent layers may be added (eg silicon dioxide) if desired. Typically the optical component is a multilayered structure of thickness in the range 0.2-10 microns. A layered structure advantageously permits layers to be in close proximity (eg a sensing waveguide and an inactive (reference) waveguide may be in close proximity to one another so as to minimise the deleterious effects of temperature and other environmental factors). Preferably, the optical component comprises a stack of transparent dielectric layers wherein layers are placed in close proximity. Preferably each layer is fabricated to allow equal amounts of electromagnetic radiation to propagate by simultaneous excitation of the guided modes in the waveguide structure. Particularly preferably the amount of electromagnetic radiation in the sensing waveguide/inactive waveguide or in the secondary waveguide/inactive secondary waveguide is equal.

The assembly may further comprise: means for intimately exposing at least a part of the optical component (eg at least a part of the (or each) sensing layer or the sensing waveguide) to the localised environment. For example, the means for intimately exposing at least a part of the optical component to the localized environment may be apart of a microstructure positionable on the surface of and intimate contact with the optical component. The microstructure may comprise means for intimately exposing at least a part of the optical component to the localized environment in the form of one or more microchannels and/or microchambers. For example, an analyte containing chemical stimuli may be fed through microchannels or chemical reactions may take place in an analyte located in a microchamber. An analyte containing chemical stimuli may be fed into the microchannels by capillary action or positively fed by an urging means. The means for intimately exposing at least a part of the optical component to the localized environment may be integrated onto the optical component.

The means for intimately exposing at least a part of the optical component to the localised environment may be adapted to induce chemical or biological changes in a static analyte containing a chemical or biological stimulus of interest. In this sense, the system may be considered to be dynamic. Chemical or biological changes (eg reactions) may be induced in any conventional manner such as by heat or radiation.

The means for intimately exposing at least a part of the (or each) sensing layer or the sensing waveguide to the localised environment may be included in a cladding layer. For example, microchannels and/or microchambers may be etched into the cladding layer. The cladding layer may perform optical functions such as preventing significant discontinuities at the boundary of the sensing waveguide or sensing layer(s) or chemical functions such as restricting access of certain species to the sensing waveguide or sensing layer(s). The cladding layer may be integrated onto the optical component.

Incident electromagnetic radiation generated by the source of incident electromagnetic radiation may be propagated into the optical component in a number of ways. For example, incident electromagnetic radiation may be input via an end face of the optical component (this is sometimes described as "an end firing procedure"). Preferably, the source of incident electromagnetic radiation provides incident electromagnetic radiation having a wavelength falling within the visible or UV range. Propagating means may be employed for substantially simultaneously propagating incident electromagnetic radiation into a plurality of waveguides. For example, one or more coupling gratings or mirrors may be used. A tapered end coupler rather than a coupling grating or mirror may be used to propagate light into the lowermost waveguide.

As a consequence of the introduction of a biological and/or chemical stimulus in the localised environment (ie a change in the refractive index of material in the localised environment), changes in the dielectric properties (eg the effective refractive index) of the optical component (eg sensing waveguide or sensing layer) occur. This causes a change in the transmission of incident electromagnetic radiation down the optical component (eg sensing waveguide (or waveguides) in whole waveguide mode or the secondary waveguide in evanescent field mode) which manifests itself as movement of the fringes in the interference pattern.

In an embodiment of the assembly, the source of incident electromagnetic radiation and one or more detectors are integrated into the assembly.

Viewed from a yet further aspect the present invention provides a method for measuring the optical activity of a stimulus of interest in a localised environment, said method comprising the steps of:
  (A) providing an assembly as hereinbefore defined;
  (B) irradiating the optical component with incident electromagnetic radiation of a first polarisation;
  (C) measuring a first characteristic of the output electromagnetic radiation;
  (D) introducing to the localised environment a stimulus of interest;
  (E) measuring a second characteristic of the output electromagnetic radiation; and
  (F) relating the change from the first characteristic of the output electromagnetic radiation to the second characteristic of the output electromagnetic radiation to the optical activity of the stimulus of interest.

In a preferred embodiment, the first and second characteristic of the output electromagnetic radiation is the intensity.

In a preferred embodiment, steps (C), (E) and (F) of the method of the invention comprise:
  (C) measuring a first interference pattern;
  (E) measuring a second interference pattern; and
  (F) relating the change from the first interference pattern to the second interference pattern to the optical activity of the stimulus of interest.

Preferably step (F) comprises: relating the intensity of at least a part of the first interference pattern relative to the intensity of at least a part of the second interference pattern to the optical activity of the stimulus of interest. Particularly preferably the intensity is the total intensity of substantially the whole of the interference pattern.

In a preferred embodiment, the method of the invention comprises:
  (A1) providing an assembly as hereinbefore defined wherein the means for relating the measurable response to the optical activity of the stimulus of interest comprises:
    an output polariser for orienting the degree of polarisation of the output electromagnetic radiation;
  (B) irradiating the optical component with incident electromagnetic radiation of a first polarisation;
  (C) measuring a first interference pattern;
  (C1) orienting the output electromagnetic radiation into a third degree of polarisation at which substantially the whole of the first interference pattern has a minimum total intensity;
  (D) introducing to the localised environment a stimulus of interest;
  (E) measuring a second interference pattern;
  (E1) orienting the output electromagnetic radiation into a fourth degree of polarisation at which substantially the whole of the second interference pattern has a minimum total intensity; and
  (F1) relating the adjustment of the output polariser required to orient the output electromagnetic radiation into the fourth degree of polarisation to the optical activity of the stimulus of interest.

In a preferred embodiment of the method, the input polariser is an input plane polariser and the output polariser is an output plane polariser.

The method may further comprise the step of:

(G) deducing from the optical activity a structural, conformational, biological or chemical property of the stimulus of interest. For example, the conformational property may be the chirality of the stimulus of interest or (where the stimulus of interest is a protein) the folding of the protein.

Steps (A) to (F) of the method of the invention may be usefully repeated at different wavelengths of incident electromagnetic radiation.

DRAWINGS

The present invention will now be described in a non-limitative sense with reference to the accompanying Figures in which.

DETAILED DESCRIPTION

Figure 1:
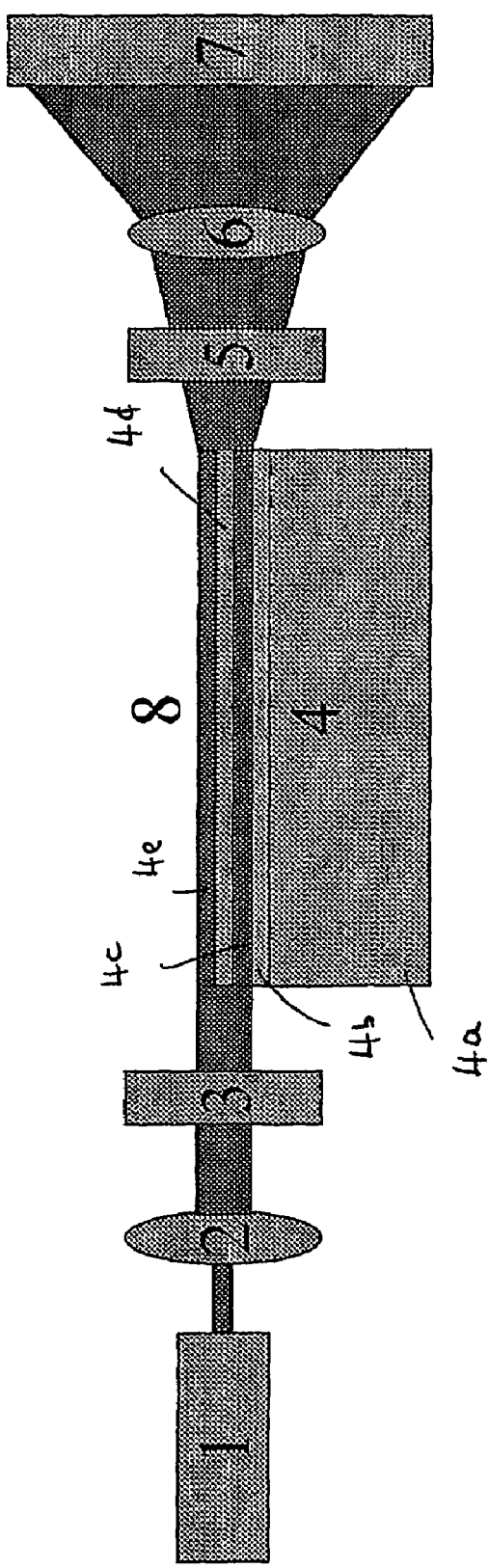
FIG. 1 illustrates schematically a first embodiment of the assembly of the invention.

FIG. 1 illustrates schematically a first embodiment of the assembly of the invention. The assembly comprises a source of incident electromagnetic radiation 1, a lens arrangement 2, an input polariser (such as a prism) 3, a planar waveguide structure 4, an output polariser (an analyser) and prism 5, a lens arrangement 6 for focussing the output electromagnetic radiation and a photomultiplier tube 7 capable of counting photons 7. The polarisation of the incident electromagnetic radiation relative to the planar waveguide structure 4 is determined by the input polariser 3.

The planar waveguide structure 4 comprises a silicon substrate layer 4a, silicon dioxide layers 4b and 4d, a silicon oxynitride layer 4c and an absorbent layer 4e. The silicon oxynitride layer 4c acts as the reference waveguide and the absorbent layer 4e acts as the sensing waveguide. The assembly is initialized by irradiating the planar waveguide structure 4 with incident electromagnetic radiation of an appropriate wavelength from the source of incident electromagnetic radiation 1 in the presence of materials which are not optically active and nulling the input polarizer 3 and output polarizer 5. The incident electromagnetic radiation is transmitted into the sensing waveguide 4e and the reference waveguide 4c simultaneously so that the level of radiation entering each is approximately the same. By ensuring that the materials in the localized environment 8 in contact with the sensing waveguide 4c are not optically active, the output electromagnetic radiation will emerge from the planar waveguide structure 4 in the same orientation. The output electromagnetic radiation is coupled into free space thereby generating an interference pattern at the photomultiplier tube 7. The output polariser 5 is aligned until the interference pattern of minimum intensity is detected by the photodetector 7. At this point, the input polariser 3 and output polariser 5 are mutually orthogonal.

The sensing waveguide 4e is exposed in the localised environment 8 to a sample (eg solution) containing the stimulus of interest which is either optically active or has the capability to be optically active. For example, the sample may be brought into contact with or bound or immobilised to the surface of the sensing waveguide 4e. The planar waveguide structure 4 is excited with the same wavelength of electromagnetic radiation as used during initialisation and the output polariser 5 is adjusted to regain the interference pattern of minimum intensity as determined by the photodetector 7. At this point the adjusted attitude of the output polariser 5 is directly proportional to the optical activity of the stimulus of interest.

Figure 2:
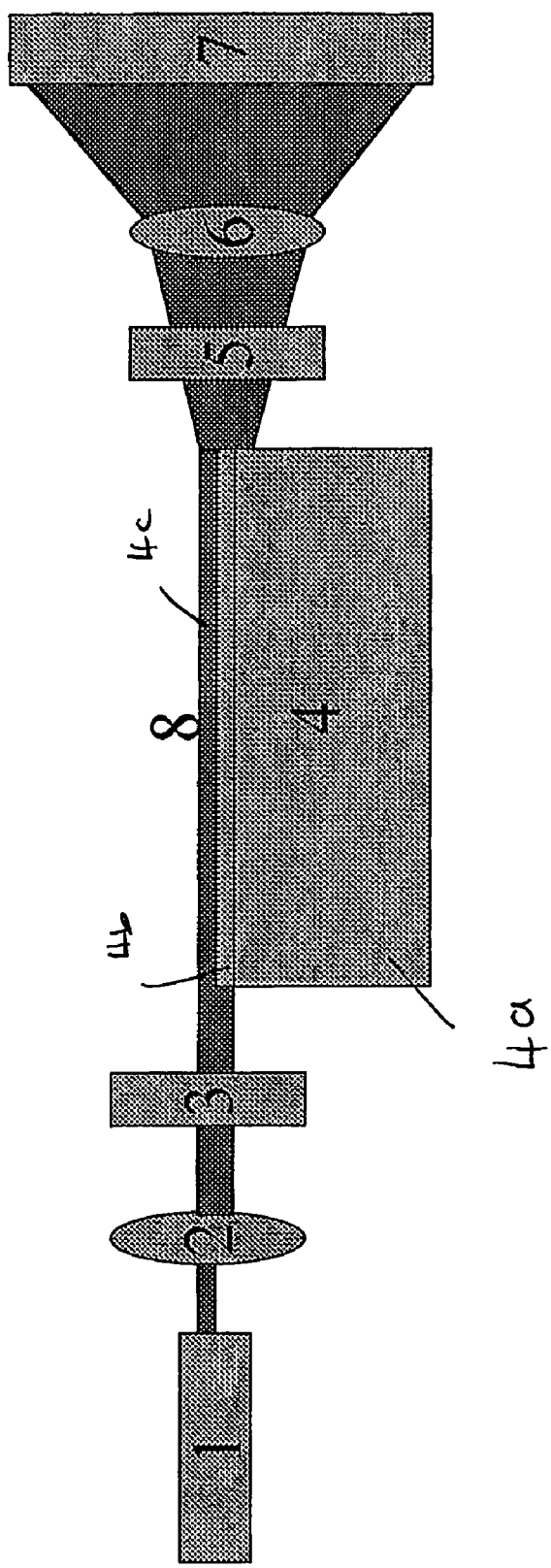
FIG. 2 illustrates schematically a second embodiment of the assembly of the invention.

FIG. 2 illustrates schematically a second embodiment of the assembly of the invention. With the exception of the planar waveguide structure 4, the assembly is identical to the first embodiment described above with reference to FIG. 1. In this embodiment, the planar waveguide structure comprises a silicon substrate layer 4a, a silicon dioxide layer 4b and an absorbent layer 4c acting as the sensing waveguide. The assembly is operated as described hereinbefore for the first embodiment.

Figure 3:
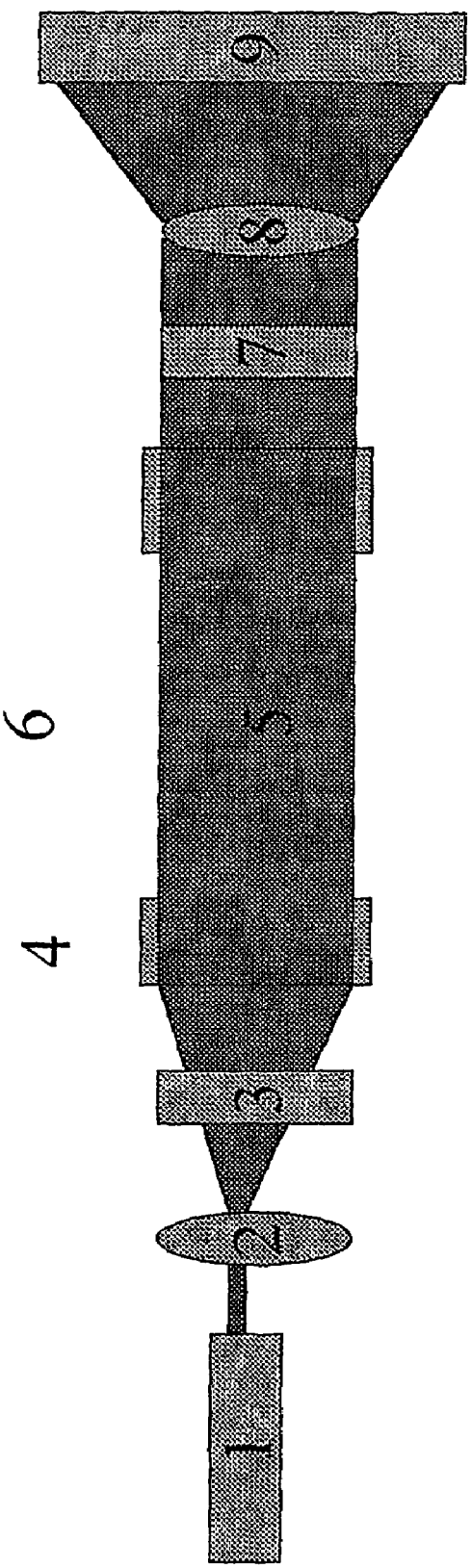
FIG. 3 illustrates schematically a third embodiment of the assembly of the invention.

FIG. 3 illustrates schematically a third embodiment of the assembly of the invention. The assembly comprises a source of electromagnetic radiation 1, a lens arrangement 2, an input polariser (such as a prism) 3, a polarisation maintaining fibre 5 with cladding 4, an output polariser (an analyser) 7 and prism, a lens arrangement 8 and a photodetector 9. The cladding 4 has been partially removed to reveal a localised environment 6 in which a stimulus of interest may be exposed to the surface of the polarisation maintaining fibre 5. The assembly is operated as described hereinbefore for the first embodiment.

The invention claimed is:

1. An assembly for measuring the optical activity of a stimulus of interest in a localised environment, said assembly comprising:

a source of incident electromagnetic radiation;

an input polariser for orienting the incident electromagnetic radiation into a first degree of polarisation;

an optical component capable of exhibiting a measurable response to a change in the degree of polarisation of the incident electromagnetic radiation into output electromagnetic radiation having a second degree of polarisation caused by the introduction of or changes in the stimulus of interest in the localised environment, wherein the optical component is an optical fibre or a waveguide structure;

means for measuring the measurable response; and means for relating the measurable response to the optical activity of the stimulus of interest.

2. An assembly as claimed in claim 1 wherein the input polariser is an input plane polariser.

3. An assembly as claimed in claim 1 further comprising: a lens arrangement capable of focussing the incident electromagnetic radiation.

4. An assembly as claimed in claim 1 further comprising: a lens arrangement capable of focussing the output electromagnetic radiation.

5. An assembly as claimed in claim 1 wherein the means for relating the measurable response to the optical activity of the stimulus of interest comprises:

an output polariser for orienting the degree of polarisation of the output electromagnetic radiation.

6. An assembly as claimed in claim 5 wherein the output polariser is an output plane polariser.

7. An assembly as claimed in claim 1 wherein the optical component is a polarisation maintaining optical component.

8. An assembly as claimed in claim 1 wherein the measurable response is or relates to a change in the intensity of the output electromagnetic radiation.

9. An assembly as claimed in claim 1 wherein the waveguide structure includes either (1) one or more sensing layers capable of inducing in a secondary waveguide a measurable response to a change in the degree of polarisation of the incident electromagnetic radiation into output electromagnetic radiation having a second degree of polarisation caused by the introduction of or changes in the stimulus of interest in the localised environment or (2) a sensing waveguide capable of exhibiting a measurable response to a change in the degree of polarisation of the incident electromagnetic radiation into output electromagnetic radiation having a second degree of polarisation caused by the introduction of or changes in the stimulus of interest in the localised environment.

10. An assembly as claimed in claim 9 wherein the waveguide structure includes one or more sensing layers capable of inducing in a secondary waveguide a measurable response to a change in the degree of polarisation of the incident electromagnetic radiation into output electromagnetic radiation having a second degree of polarisation caused by the introduction of or changes in the stimulus of interest in the localised environment.

11. An assembly as claimed in claim 10 wherein the optical component further comprises: an inactive secondary waveguide in which the sensing layer is substantially incapable of inducing a measurable response to a change in the degree of polarisation of the incident electromagnetic radiation into output electromagnetic radiation having a second degree of polarisation caused by the introduction of or changes in the stimulus of interest in the localised environment.

12. An assembly as claimed in claim 9 wherein the waveguide structure includes a sensing waveguide capable of exhibiting a measurable response to a change in the degree of polarisation of the incident electromagnetic radiation into output electromagnetic radiation having a second degree of polarisation caused by the introduction of or changes in the stimulus of interest in the localised environment.

13. An assembly as claimed in claim 12 wherein the optical component further comprises: an inactive waveguide substantially incapable of exhibiting a measurable response to a change in the degree of polarisation of the incident electromagnetic radiation into output electromagnetic radiation having a second degree of polarisation caused by the introduction of or changes in the stimulus of interest in the localised environment.

14. An assembly as claimed in claim 9 wherein each waveguide of the waveguide structure is a planar waveguide.

15. A method for measuring the optical activity of a stimulus of interest in a localised environment, said method comprising the steps of:
(A) providing an assembly as defined in any preceding claim;
(B) irradiating the optical component with incident electromagnetic radiation of a first polarisation;
(C) measuring a first characteristic of the output electromagnetic radiation;
(D) introducing to the localised environment a stimulus of interest;
(E) measuring a second characteristic of the output electromagnetic radiation; and
(F) relating the change from the first characteristic of the output electromagnetic radiation to the second characteristic of the output electromagnetic radiation to the optical activity of the stimulus of interest.

16. A method as claimed in claim 15 wherein the first and second characteristic of the output electromagnetic radiation is the intensity.

17. A method as claimed in claim 15 wherein steps (C), (E) and (F) comprise:
(C) measuring a first interference pattern;
(E) measuring a second interference pattern; and
(F) relating the change from the first interference pattern to the second interference pattern to the optical activity of the stimulus of interest.

18. A method as claimed in claim 17 wherein step (F) comprises: relating the intensity of at least a part of the first interference pattern relative to the intensity of at least a part of the second interference pattern to the optical activity of the stimulus of interest.

19. Method as claimed in claim 18 wherein the intensity is the total intensity of substantially the whole of the interference pattern.

20. A method as claimed in claim 15 comprising:
(A1) providing an assembly as defined in any of claims 1 to 16 wherein the means for relating the measurable response to the optical activity of the stimulus of interest comprises:
an output polariser for orienting the degree of polarisation of the output electromagnetic radiation;
(B) irradiating the optical component with incident electromagnetic radiation of a first polarisation;
(C) measuring a first interference pattern;
(C1) orienting the output electromagnetic radiation into a third degree of polarisation at which substantially the whole of the first interference pattern has a minimum total intensity;
(D) introducing to the localised environment a stimulus of interest;
(E) measuring a second interference pattern;
(E1) orienting the output electromagnetic radiation into a fourth degree of polarisation at which substantially the whole of the second interference pattern has a minimum total intensity; and
(F1) relating the adjustment of the output polariser required to orient the output electromagnetic radiation into the fourth degree of polarisation to the optical activity of the stimulus of interest.

21. A method as claimed in claim 20 wherein the input polariser is an input plane polariser and the output polariser is an output plane polariser.

22. A method as claimed in claim 15 further comprising the step of:
(G) deducing from the optical activity a structural, conformational, biological or chemical property of the stimulus of interest.

23. A method as claimed in claim 22 wherein the conformational property is the chirality of the stimulus of interest or (where the stimulus of interest is a protein) the folding of the protein.

* * * * *